(12) United States Patent
Salter et al.

(10) Patent No.: US 6,590,030 B2
(45) Date of Patent: Jul. 8, 2003

(54) ANIONIC ALKOXYLATE SURFACTANT

(75) Inventors: Elizabeth Ann Salter, Richmond (AU); Patrick William Houlihan, Wheelers Hill (AU); Michael Anthony Bajraszewski, Keilor East (AU); Rodney Walter Parr, Doncaster (AU); Keith Moody, Watsonia North (AU)

(73) Assignee: Orica Australia Pty Ltd, Melbourne (AU)

( * ) Notice: Subject to any disclaimer, the term of this patent is extended or adjusted under 35 U.S.C. 154(b) by 54 days.

(21) Appl. No.: 09/924,597

(22) Filed: Aug. 9, 2001

(65) Prior Publication Data

US 2002/0061828 A1 May 23, 2002

Related U.S. Application Data

(62) Division of application No. 09/485,186, filed as application No. PCT/AU98/00620 on Aug. 6, 1998, now Pat. No. 6,335,314.

(30) Foreign Application Priority Data

Aug. 8, 1997 (AU) ............................................. PO 8462

(51) Int. Cl.[7] ............................ C08K 5/09; C08K 5/41; C08K 5/51; C08K 5/06; C08K 2/00
(52) U.S. Cl. ........................ 524/776; 524/710; 524/713; 524/745; 524/760; 526/209
(58) Field of Search ................................. 524/776, 710, 524/713, 745, 760; 526/209

(56) References Cited

U.S. PATENT DOCUMENTS

| | | |
|---|---|---|
| 4,721,581 A | 1/1988 | Ramachandran et al. |
| 4,830,764 A | 5/1989 | Wiedemann |
| 4,939,283 A | 7/1990 | Yokota et al. |
| 5,653,988 A | 8/1997 | Gerber et al. |
| 5,691,299 A | 11/1997 | Fabry |

FOREIGN PATENT DOCUMENTS

| | | |
|---|---|---|
| DE | 4443643 A1 | 8/1994 |
| JP | 97-420564 | 7/1997 |
| WO | WO 91/13849 | 9/1991 |
| WO | WO 93/03007 | 2/1993 |

OTHER PUBLICATIONS

JP 09–188661 A (KAO CORP), Jul. 22, 1997 abstract.

*Primary Examiner*—Tae H. Yoon
(74) *Attorney, Agent, or Firm*—Pillsbury Winthrop LLP

(57) ABSTRACT

This invention relates to an anionic alkoxylate surfactant of formula (I), where R is a di- or tri-unsaturated $C_{4-22}$ straight or branched hydrocarbon chain, at least two double bonds of said unsaturated chain being conjugated and exhibiting opposite geometric isomerism; m is 0 or 1; Y is O or NR'; each R' is independently selected from hydrogen, $C_{1-6}$ alkyl and phenyl; n is 1 to 50; and OX is an anionic group selected from the group consisting of acids or salts of sulfate, phosphate, sulphosuccinate, succinate, carbomethyl, maleate, carboxyethyl, alkenylsuccinate, phthalate, sulphoethyl, 3-sulpho-2-hydroxypropyl, sulphopropyl, oxalate and citrate.

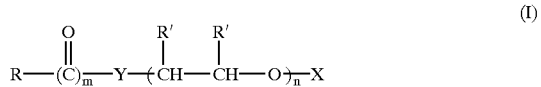

16 Claims, No Drawings

ANIONIC ALKOXYLATE SURFACTANT

CROSS REFERENCE TO RELATED APPLICATIONS

This application is a divisional application of U.S. Ser. No. 09/485,186, filed Mar. 21, 2000, which further claims priority from International Application No. PCT/AU98/00620. These applications, in their entirety, are incorporated herein by reference.

This invention relates to anionic alkoxylate surfactants and to their use in preparing aqueous polymeric dispersions.

Nonionic alkoxylate surfactants have been known for many years and they have been used in many industrial applications including the preparation of aqueous polymeric dispersions. These non-ionic alkoxylate surfactants typically consist of a hydrophobic portion or chain which is covalently bonded to a poly(oxyalkylene) chain, especially poly(oxyethylene), which provides the hydrophilic portion of the surfactant.

WO91/13849, the entire contents of which is incorporated by reference, discloses fatty alcohol alkoxylate surfactants in which the fatty alcohol chains contain a pair of conjugated double bonds having opposite geometric isomerism which are reactive in dispersion polymerisation. These surfactants are described as being useful as stabilisers in the preparation of aqueous dispersions of film forming addition polymers.

In certain aqueous dispersions of polymerisation preparations the solely nonionic characteristics of these stabilisers means that relatively high levels of stabilisers are required to be used to prepare the desired fine particle size aqueous dispersions. This may add to the raw material costs of such dispersions and/or cause a degradation in resulting film properties, especially properties associated with high levels of water soluble species such as early water resistance. The solely nonionic character may also result in limitations in processing conditions. For example, with this class of surfactants lower temperature polymerisation is often required to provide dispersions with low levels of coagulum. These lower temperatures may result in extended processing time and hence increased manufacturing costs.

The use of small amounts of anionic surfactants in combination with these prior-art non-ionic stabilisers is capable of producing the desired small particle size dispersions while maintaining the desired low levels of non-ionic stabiliser. However, these polymer dispersions suffer from problems commonly associated with the use of conventional anionic surfactants. These include residual water sensitivity in films formed from such aqueous dispersions, intolerance to polyvalent species and foaming.

The alkylphenol hydrophobe has exceptional adsorption onto hydrophobic surfaces and therefore generally has superior performance to aliphatic analogues. Alkylphenol ethoxylate non-ionic surfactants have been previously converted to anionic sulfates or phosphates and this class of surfactant has been known for several years. However, this class of anionic alkoxylates can also lead to residual water sensitivity in films formed from aqueous film forming dispersions prepared with this class of surfactants as stabilisers. Additionally, alkylphenol ethoxylates are thought to be environmentally unfavourble due to their poor biodegradability and subsequent aquatic toxicity.

Anionic alkoxylate surfactants are claimed in U.S. Pat. No. 4,939,283 by Yokota et al. These surfactants are typically prepared by reacting a hydrophobe such as nonylphenol (1 mole) with allyl glycidyl ether (1 mole) and condensing ethylene oxide (10–50 moles). The terminal hydroxyl is then converted to the sulphate ester, phosphate ester, sulfosuccinate half ester or sulfosuccinate diester. Salts of these species are included and these are the alkali metal, ammonium and low alkanolamine salts. These surfactants offer some improvement in colloidal stability. However, in certain applications they appear to be less useful and it is speculated that this may attribute to the relatively low reactivity of the meth(allyl) unsaturated group in certain copolymerisation reactions.

It is an object of the present invention to overcome or at least alleviated one or more of the problems associated with the stabilisers described in the prior art.

Accordingly the present invention provides an anionic alkoxylate surfactant of the formula I

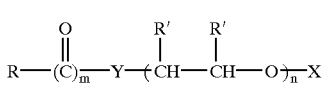

where R is a di- or tri-unsaturated $C_{4-22}$ straight or branched hydrocarbon chain, at least two double bonds of said unsaturated chain being conjugated and exhibiting opposite geometric isomerism;

m is 0 or 1;

Y is O or NR';

each R' is independently selected from hydrogen, $C_{1-6}$ alkyl and phenyl; n is 1 to 50; and OX is a anionic group selected from the group consisting of acids or salts of sulphate, phosphate, sulphosuccinate, succinate, carboxymethyl, maleate, carboxyethyl, alkenylsuccinate, phthalate, sulphoethyl, 3-sulpho-2-hydroxypropyl, sulphopropyl, oxalate and citrate.

Preferably the surfactant has an R group of the following structure:

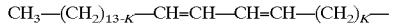

where K is 8 or 9.

Preferably R is a surfactant accordingly to claim 1 wherein R is derived from linoleyl or linolenyl alcohol or acid by alkoxylation of said alcohol or acid.

The

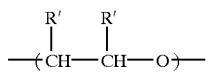

units may be the same or different.

Preferably at least one R' on the or each —(CHR'—CHR'—O)— unit is hydrogen. More preferably both R' on the or each —(CHR'—CHR'—O)— unit are hydrogen.

Preferably OX is sulphate, phosphate, sulphosuccinate, carboxymethyl or a salt thereof.

Preferably the salt is an amine, ammonium or alkali metal salt.

The surfactant of formula I is preferably derived from a fatty alcohol such that m is 0. The surfactant may also be derived from fatty acid esters, fatty amines, and fatty acid amides. Where Y is NR', R' is preferably H or $CH_3$.

The invention provides in an alternative form an aqueous dispersion of polymeric particles wherein the dispersion is formed in the presence of a stabilising amount of anionic alkoxylate surfactants as described above.

Preferably the polymer dispersion is prepared by addition polymerisation of addition polymerisable monomer. Preferably the addition polymerisable monomer is an ethylenically unsaturated monomer.

Preferably the polymer dispersion is film forming at or near ambient temperature with the optional use of external plasticisers.

The aqueous dispersion may also be prepared by dispersion of a condensation polymer.

The invention also provides the use of an anionic surfactant as described above as a stabiliser in the preparation of an aqueous dispersion of polymeric particles, or as a substitute for alkylphenol based surfactants in the preparation of aqueous dispersion of polymeric particles and coating compositions.

DETAILED DESCRIPTION OF THE INVENTION

The anionic alkoxylate surfactants of the present invention can be prepared by first forming alkoxylate product on a suitable hydrocarbon chain and then converting the hydroxyl group to an appropriate anionic species. Preferred hydrocarbon chains are the fatty chains of unsaturated fatty alcohols. The preferred alkylene oxides are ethylene oxide.

As well, as for example, condensing fatty alcohol with ethylene oxide, other alkylene oxides can be used either alone or as a mixture. For example, a random co-polymer of ethylene and propylene oxide can be used. Alternatively a block alkoxylate copolymer could be prepared by first reacting a fatty alcohol with, for example, propylene or butylene oxide and then condensing this adduct with ethylene oxide. Similar alkoxylation products can be obtained from the corresponding esters, amines and amides.

The fatty alcohols that are preferred are the C18 fatty alcohols, linoleyl and linolenyl alcohols. Other fatty alcohols and or the corresponding fatty acids can be used. In certain embodiments fatty amines and fatty amides may be used as the hydrophobe of the surfactants. Fatty alcohols of other chain lengths may be used, the most preferred having 10–22 carbon atoms. The corresponding carboxylic acids, etc. are also suitable.

The poly(oxyalkylene) chain length of the surfactant corresponds to that from 1–50 alkylene oxide units. The nature of the individual units is very much determined by the end use to which the compound will be put. For example, if the compound is to be a reactive surfactant in an aqueous emulsion polymerisation system, the poly(oxyalkylene) chain will consist mainly, and preferably solely, of poly (oxyethylene) units. Provided that the desired balance between the lipophilic and hydrophilic portions of the surfactant can be achieved, it is possible to include a proportion of oxypropylene, oxybutylene or oxyphenylethylene units. These are advantageously located on the chain adjacent to the lipophilic portion as they increase the overall lipophilcity of the molecule. However they may be arranged in the opposite fashion. It is important to note that the overall character of the surfactant is determined after the anionic species is introduced. Compared with wholly non-ionic surfactants generally shorter hydrophilic chains are possible as well as slightly less hydrophilic poly(oxyalkylene) chains. The preferred poly(oxyalkylene) unit is the poly (oxyethylene) unit and preferably all of the poly (oxyalkylene) units are poly)oxyethylene) units.

The compounds of this invention may be synthesised by any convenient means. A particularly useful method of preparing the precursors to the preferred compounds is the reaction of alkylene oxide with a fatty alcohol in the presence of a base catalyst which is a Bronsted base.

It will be readily appreciated that in the case of linoleyl alcohol the structure of this alcohol is different to that of the non-oxyalkylene chain part of the surfactant compounds; linoleyl alcohol is cis-9, cis-12-octadecadienol. As described in WO91/13849, under alkoxylation conditions, one of the double bonds positioned at the 9- or the 12-position transfers into a conjugated arrangement with respect to the other, and at the same time this bond changes its stereochemical configuration such that there is one cis-bond and one trans-bond.

The linoleyl alcohol for use in this preferred aspect of the invention maybe a pure substance. Alternatively, it is possible to use one of the commercially-available mixtures of fatty alcohols which contain a significant proportion of linoleyl alcohol. It has been found that the alkoxylation of such mixtures can give a product which is acceptable for many uses and which is considerably cheaper than using pure linoleyl alcohol. Examples of suitable commercially-available mixtures can be found in the "Ocenol" range of product of Henkel KGaA, one suitable one being the "110–130" grade.

By "Bronsted base" is meant a base which is capable of abstracting a proton. While any Bronsted base will work to some extent in the invention it will readily be appreciated by the skilled worker that, for some bases, the obtaining of acceptable yields will require unacceptably long reaction times and/or unacceptably severe reaction conditions, and the use of such bases is not therefore a practical proposition. As a general rule, reaction times should be no longer than 48 hours and reaction conditions no more severe than 160° C. temperature and 1000 kPa pressure. Any Bronsted base which gives an acceptable yield under conditions such as these is especially preferred for use in this invention. Examples of preferred bases are the alkali metal and alkaline earth metal alkoxides and hydroxides, particularly sodium methoxide and potassium hydroxide. Other suitable bases include metal hydrides, such as sodium hydride.

The anionic species may be introduced into the surfactant precursor in a number of ways. It is important that the method selected does not cause the unsaturation in the hydrophobe to be altered or such that it no longer remains within the scope of Formula I. Examples of suitable methods are as follows:

Phosphate ester derivatives can be made by reaction of the alkoxylate species with either phosphorous pentoxide or polyphosphoric acid. The former result in a mixture of mono- and di-alkyl phosphate derivatives whereas the latter gives primarily the monoalkyl derivative; the corresponding salts can be prepared from the acid form of the phosphate by neutralisation with, for example, alkali metal hydroxides or ammonia.

Sulphate esters are preferably made with sulfamic acid as the sulfating reagent: the ammonium salt of the sulphate will be initially formed and this can be converted into an alkali metal salt, if required, by reaction with an alkali metal hydroxide, with release of ammonia: sulphur trioxide is an alternative sulfating reagent but this may result in reaction with the double bond system of the hydrophobe and is not preferred. Carboxymethyl derivatives of the alkoxylate species can be made by reaction with sodium chloracetate in the presence of base. Succinates, maleates, phthalates and alkenylsuccinates can be prepared by reaction of the alkoxylate with the corresponding anhydride: neutralisation of this condensate with alkali metal hydroxides or ammonia provides the corresponding salts. Further reaction of the maleate with sodium bisulphite leads to the sulphosuccinate derivatives. The methods of U.S. Pat. No. 4,939,283 are also incorporated by reference.

Aqueous polymeric dispersions using the surfactants of the present invention can be prepared by addition polymerisation of ethylenically unsaturated monomers. Alternatively the polymer dispersion may be a condensation polymer such as an alkyd resin prepared from drying to semi-drying vegetable oil. In the case of an alkyd resin a hot melt mixture of the surfactant and alkyd resin can be prepared and emulsification in water can be carried out by addition to water under mechanical agitation. Phase inversion techniques are also able to be used whereby water is added under agitation to the melt until phase inversion takes place. In addition ultrasonic and other known methods of emulsification can be used. It is believed that the unsaturated groups on the hydrophobic portion of the surfactants of the present invention participate in autoxidation reactions with other surfactant molecules and/or the alkyd resin to give film properties with improved hardness. This is believed to occur because the surfactant covalently bonds to the polymeric dispersion.

As stated above the polymer dispersion may be prepared from addition polymerisable ethylenically unsaturated monomers.

The nature of the unsaturated monomer is not narrowly critical and particles may be prepared by this process using a wide range of monomers commonly used in suspension and emulsion polymerisation, for example, one or more of the monomers selected from the group of the $C_{1-12}$ (preferably the $C_{1-4}$) alkyl acrylates and methacrylates, (meth)acrylates and methacrylates, butyl methacrylate, stearyl methacrylate, methacrylic acid, methoxypropyl methacrylate, cyclohexyl methacrylate, benzyl methacrylate, hydroxyethyl methacrylate, hydroxypropyl methacrylate, dimethylaminoethyl methacrylate, N-butoxymethyl methacrylamide, N-butoxymethyl acrylamide, glycidyl methacrylate, vinyl acetate, vinyl propionate, styrene and vinyl styrene, vinyl toluene, methoxy styrene and vinyl pyridine, di-butyl maleate and vinyl chloride.

The known techniques of suspension and emulsion polymerisation, including the selection of appropriate polymerisation initiators, are applicable to the preparation of the aqueous dispersions of this invention. As is understood in the art polar monomers may need to be used in combination with less polar monomers to achieve suitable aqueous polymeric dispersions. Either thermally activated or redox initiators may be used.

Due to the reactivity of the compounds of Formula I they have been found to provide a particularly stable dispersion of polymer particles therefore providing a significant improvement in aqueous coating compositions.

The aqueous dispersion may comprise additives which adapt it for use as a coating composition.

Coating compositions may be prepared by blending standard additives such as pigments, extenders, antifoams, thickeners and fungicides into the dispersion in art-recognised quantities using known methods.

An example of polymer particles which may be produced using the compounds of Formula I is described in U.S. Pat. No. 4,413,073.

A further preferred example of polymer particles which may be prepared using compounds of Formula I are core-sheath particles of the type described in Australian Patent Application No. 52006/90. Such particles will have diameters of less than 100 nm and comprise a core of polymer of an ethylenically unsaturated monomer and a sheath comprising poly(oxyalkyene) chains are derived from the covalent bonding of compounds of Formula I with the core addition-polymer.

The invention will be further described by reference to the following non-limiting examples in which all parts are expressed by weight.

EXAMPLE 1

This example shows the preparation of a Ocenol 110–130 ethoxylate (10 moles) phosphate, acid forming, according to the invention.

A fatty alcohol ethoxylate was prepared by condensing with 10 moles of ethylene oxide per mole of fatty alcohol.

616 parts of "Ocenol" (Trade Mark) 110–130 (ex Henkel KGaA), (a commercially-available mixture of fatty alcohols being approximately 40% by weight linoleyl alcohol) was warmed to dissolve any separated components. It was then charged to an autoclave and purged with nitrogen. There was then slowly added 18 parts of 30% sodium methoxide. The vessel containing the sodium methoxide was rinsed three times with 15 parts ethanol and this ethanol slowly charged with stirring. The autoclave was evacuated, purged with nitrogen and then evacuated and heated to 130° C., all volatile materials being stripped off. The evacuation and purging with nitrogen was repeated and 1034 parts ethylene oxide was then added over a period of 2 hours, the autoclave being maintained at 130° C.–145° C. and 100–500 ka pressure. Reaction was continued for 30 minutes, and the contents of the autoclave were then cooled and volatiles were stripped off under vacuum to leave the desired product.

To the Ocenol 110/130 10EO adduct (190.5 g) was added phosphorous pentoxide (16.0 g) using a Silverson mixer with ice cooling to cool the mixture. The mixture was maintained at less than 50° C. while the phosphorous pentoxide was added over 20 minutes. The mixture was continued to be stirred under high shear for a further 30 minutes at 60–70° C. The reaction product was then transferred to flanged top flask and heated under gentle stirring for 3 hours at 95° C. Water (12.2 g) was added to the reaction mixture and the mixture was heated for 2.5 hrs at 100° C. and then the water was removed under vacuum and heating to 103° C. The water content of the final product of 0.18% and the acid value of the final product was 114 mg KOH/g. The phosphoric acid content was 0.102 mmoles/g and the ratio of di- to mono-alkyl phosphate ester species was 0.29 by $^{13}C$—NMR.

EXAMPLE 2

This example shows the preparation of additional Ocenol 110–130 adducts with 6 and 30 moles of ethylene oxide according to the invention.

These products were prepared using the procedure described in Example 1 with the addition of the requisite amount of ethylene oxide to attain target molecular weight. The hydroxyl value measured on the 6 and 30 mole adducts were 116 mgKOH/g and 44 mgKOH/g respectively.

EXAMPLE 3

This example shows the preparation of an Ocenol 110–130 ethoxylate (30 moles) sulfate, sodium salt according to the invention. The Ocenol 110–130 ethoxylate (30 moles) (300 g) as prepared in Example 2 wad added to a one liter reactor and heated to 100° C. under nitrogen and dehydrated to 0.05% w/w water by using vacuum and nitrogen purge. Urea (1.4 g) was charged to the reactor and allowed to dissolve into the reaction mix over 5 minutes. Sulfamic acid (25.1 g) was added over 45 minutes with the temperature maintained at 100° C. The temperature was maintained at 100° C. for a further two hours and then the reaction mixture was cooled to 50° C. A 46% w/w NaOH solution (25.0 g) was added and the reaction mixture was heated to 100° C. to accelerate the release of ammonia to form the sodium salt of the sulfate. The yield of the Ocenol 110–130 ethoxylate (30 moles) sulfate, sodium salt, was 89% w/w was measured by two-phase titration. The final product was then cooled. Preservation of the unsaturation was confirmed by iodine value.

EXAMPLE 4

This example shows the preparation of the Ocenol 110–130 ethoxylate (6 moles) sulfate, ammonium salt, according to the invention.

The adduct (100 g) was converted to the sulfate as described in Example 3 using urea(1.13 g) and sulfamic acid (21.0 g). The sulfate was left in the ammonium salt form and residual sulfamic acid neutralised with monoethanolamine (2.31 g). The yield of the sulfated adduct was 88.5% w/w by two-phase titration.

EXAMPLE 5

This example shows the preparation of stearyl alcohol ethoxylates with 5, 10 and 30 moles of ethylene oxide.

These three materials were made by reaction of stearyl alcohol with the appropriate amount of ethylene oxide using a similar procedure to that described in Example 1 but using potassium hydroxide as catalyst. The three ethoxylates were made in the one batch, withdrawing samples of the 5 and 10 mole ethoxylates en route to the 30 mole adduct. The raw material and catalyst was dehydrated at 120° C. for 1.5 hr. prior to addition of ethylene oxide at 150° C. The base catalyst in the ethoxylates was neutralized with acetic acid after completion of the reaction. The hydroxyl value of the three products was 118.3, 76.6 and 35.5 mgKOH/g, corresponding to 4.6, 10.5 and 29.8 mole adducts respectively. Water content was <0.03% w/w.

EXAMPLE 6

This example shows the preparation of a stearyl alcohol ethoxylate (5 moles) phosphate, acid form.

The stearyl alcohol ethoxylate (170.7 g) was phosphated with phosphorous pentoxide (21.3 g) using a procedure similar to that described in Example 1. The phosphation was completed by heating at 96–97° C. for 4 hr before adding water (16.2 g) and heating for a further 3 hr. The product was dehydrated to final water content of 0.1% w/w. The total acid value of the phosphate was 151.5 mgKOH/g, the phosphoric acid content 0.168 mmoles/g and the mole ratio of di- to monoalkyl phosphate esters was 0.40 by $^{13}C$—NMR.

EXAMPLE 7

This example shows the preparation of a stearyl alcohol ethoxylate (10 moles) phosphate, acid form.

The stearyl alcohol ethoxylate (175.8 g) was phosphated with phosphorous pentoxide (14.2 g) using a procedure similar to that described in Example 1. Phosphation was completed by reaction at 99° C. for 5.75 hr before adding water (10.8 g) and continuing heating for 2.25 hr. The product was dehydrated to water content of 0.13% w/w. The total acid value of the phosphate was 102.3 mgKOH/g, the phosphoric acid content 0.131 mmoles/g and the mole ratio of mono- to dialkyl phosphate esters was 0.44 by $^{13}C$—NMR.

EXAMPLE 8

This example shows the preparation of the stearyl alcohol ethoxylate (5 moles) sulfate, ammonium salt.

The adduct (300 g) was converted to the sulfate as described in Example 3 using urea(3.78 g) and sulfamic acid (67.5 ). The sulfate was left in the ammonium salt form and residual sulfamic acid neutralised with monoethanolamine (5.79 g). The yield of the sulfated adduct was 90.5% w/w by two-phase titration.

EXAMPLE 9

This example shows the preparation of the stearyl alcohol ethoxylate (30 moles) sulfate, sodium salt.

The adduct (400 g) was converted to the sulfate as described in Example 3 using urea(1.52 g) and sulfamic acid (27.01 g). As in Example 3 the sodium salt of the sulfate was formed by the addition of 30% w/w NaOH solution (42.52 g) and subsequent release of ammonia. The yield of the sulfated adduct was 90.6% w/w by two-phase titration.

EXAMPLE 10

This example illustrates the preparation of an aqueous addition polymer dispersion using the surfactant of Example 1.

The materials and quantities used were as follows:

| Stage | | |
|---|---|---|
| A | demineralised water | 567.00 parts |
| B | surfactant (Example 1) 10% w/w concentration in water neutralised to pH 9 with ammonia | 20.00 |
| C | butyl acrylate | 11.75 |
|   | methyl methacrylate | 13.00 |
|   | methacrylate acid | |
| D | potassium persulphate | 1.00 |
|   | demineralised water | 25.00 |
| E | methyl methacrylate | 508.25 |
|   | butyl acrylate | 457.00 |
|   | methacrylic acid | 9.75 |
|   | demineralised water | 443.00 |
|   | surfactant (Example 1) 10% w/w concentration in water neutralised to pH 9 with ammonia | 100.00 |
| F | demineralised water | 4.00 |
|   | potassium persulfate | 125.00 |

Stage A was added to a 3 liter reaction vessel (equipped with mechanical stirrer) and stirred under nitrogen for about 10 minutes while heating to 80 C.

Stage B was added to the reaction vessel and the nitrogen purge was stopped.

Stage C was added and mixed for 10 minutes.

Stage D was premixed and then added to the reaction vessel at 80 C. and the reaction mixture was allowed to exotherm to 85 C. and it was maintained at this temperature.

Stages E and F were individually premixed and separately but concurrently fed over a 3 hour period. Stage E was a coarse emulsion. After the feeds were completed the reaction vessel was maintained at 85 C. for two hours and then allowed to cool to 30 C. before neutralisation with ammonia and filtration. The solids of the resultant latex was 45.0% w/w and the wet coagulum collected from filtration was 0.023%. The surface tension of the latex product was 54.1 mN/m.

EXAMPLE 11

This is a comparative example which shows the adverse consequent if a surfactant not according to the invention is used.

A latex was prepared as in Example 10 except that there was a w/w replacement of the surfactant used with the non-phosphated version of that surfactant prepared as an intermediate in Example 1. The level of coagulum was 10 times greater than in Example 10 and the particle size was visually noted to be significantly larger and it was concluded that this latex was therefore relatively poor.

EXAMPLE 12

This example illustrates the preparation and performance of aqueous addition polymers using the surfactants of Example 4 and Example 8 compared to a commercially available surfactant based on nonylphenol as the hydrophobe.

The materials and quantities used were as follows:

| Stage A | demineralised water | 439.68 parts |
| --- | --- | --- |
|  | surfactant | 7.00 |
| B | sodium carbonate | 0.36 |
|  | ammonium persulphate | 0.28 |
|  | demineralised water | 1.94 |
| C | demineralised water | 76.72 |
|  | ammonium persulphate | 3.94 |
|  | sodium carbonate | 0.68 |
| D | demineralised water | 226.60 |
|  | surfactant | 7.00 |
|  | acrylic acid | 8.65 |
|  | methyl methacrylate | 196.16 |
|  | butyl acrylate | 167.01 |
|  | styrene | 71.88 |
| E | demineralised water | 61.16 |
| F × 3 | tertiary butyl perbenzoate | 0.66 |
|  | demineralised water | 0.62 |
| G × 3 | sodium erythorbate | 0.32 |
|  | demineralised water | 3.20 |
| H | ammonia adjustment | 9.72 |
|  | demineralised water | 9.72 |
| I | "Bevaloid" (Trade Mark) | 0.20 |
|  | demineralised water | 10.00 |
| J | "Proxel" (Trade Mark) | 1.60 |
|  | demineralised water | 8.00 |

Stage A was added to the reaction vessel (equipped with mechanical stirrer) and stirred under nitrogen for 30 minutes at 80° C.

Stage D monomer emulsion was formed by preheating water and surfactant to 60° C. and adding of monomers in order with vigorous stirring.

Premixed B stage was added to the rector and held for 10 minutes.

C and D stages were fed into the reactor simultaneously but separately over a 4 hour period.

The feeds were washed out with E stage, and the mixture held for 15 minutes. Premixed F and G stages were then added and the mixture held for 30 minutes.

F and G stage additions were repeated twice and premixed H stage was added. The mixture was held for 15 minutes and then I stage was added.

The latex was cooled to below 40° C. and then J stage was added.

A series of three latexes were produced to the above formulation by replacing the surfactant on a weight for weight basis.

|  | Surfactant | |
| --- | --- | --- |
| Sample A | Nonylphenol ethoxylate (5 moles) sulphate | Rhodapex (Trade Mark) CO436 |
| Sample B | Ocenol ethoxylate (6 moles) sulphate | Example 4 |
| Sample C | Stearyl ethoxylate (5 moles) sulphate | Example 8 |

An indication of the usefulness of a particular surfactant in the polymerisation recipe can be the level of instability during processing leading to the formation of gel bits or coagulum which must be filtered out of the finished product. Excessive coagulum can be a substantial production problem leading to long filtration times and loss of productivity.

Another measure of the ability of the surfactant to stabilise the polymer particles in the comparative stability of the disperison to the addition of electrolyte. The surfactant (Example 4) shows enhanced stability to added electrolyte which we attribute to the presence of the reactive nature of the hydrophobe.

A final measure of the ability of surfactants to become bound into the final film is the water resistance of the final film. Where a surfactant is inadequately adsorbed or bound to the particle surface there is a tendency for it to be easily resolvated by water with the result that the final film containing the surfactant will show a lower level of performance.

The following table illustrates the advantage given by surfactants produced according to the invention in each of these performance areas.

|  | Coagulum % w/w on finished product | Electrolyte Tolerance* | Water Soak Test** |
| --- | --- | --- | --- |
| Sample A | 0.1 | Coagulation | 3 hrs Slight cloudiness |
| Sample B | 0.01 | Stable | Overnight Slight cloudiness |
| Sample C | 0.13 | Coagulation | Completely white opaque film |

*Addition of 5g of 10% NaCl to 5g of latex.
**Film drawdown over a alkyd enamel sealed surface and dried for three hours. Film then is soaked in cold water overnight.

EXAMPLE 13

This example illustrates the performance of aqueous addition polymers produced using the phosphate derivative surfactants Example 1 and Example 7. As with the previous example, a commercial source of nonylphenol ethoxylate (10 moles) phosphate surfactant ie. Alkanate (Trade Mark) PA100 has been included.

Latexes were prepared as in Example 10 by using the following procedure;

Stages A and B were added to the reactor and stirred while heating to 80° C. The vessel was purged with nitrogen for at least 20 minutes.

Stage C was added and the mixture stirred for 10 minutes.

Stage D was premixed and added to the reactor.

After holding for 20 minutes, premixed stages E and F were added simultaneously but separately to the reactor over 3 hours.

At the end of the feed, the mixture was held at 85° C. for 2 hours. The pH was adjusted and the latex cooled to less than 30° C.

A series of latexes were produced using the above formulation but replacing the surfactant with the following on a weight for weight basis.

|  | Surfactant |  |
|---|---|---|
| Sample E | Nonyl phenol ethoxylate (10 moles) phosphate | Alkanate PA100 |
| Sample F | Ocenol ethoxylate (10 moles) phosphate | Example 1 |
| Sample G | Stearyl ethoxylate (10 moles) phosphate | Example 7 |

The latexes were compared in a similar range of performance tests to the sulphate derivatives of Example 12.

|  | Water Soak Test | Adhesion | Particle Diameter DN (nm) | Particle Diameter DW (nm) | pH of Latex |
|---|---|---|---|---|---|
| Sample E | 3 | 2 | 132 | 141 | 5.4* |
| Sample F | 1 | 1 | 107 | 122 | 7.7 |
| Sample G | 2 | 3 | 114 | 128 | 7.5 |

1 = best 3 = worst
*pH adjusted prior to testing

The film test shows the clear advantage of surfactant produced in accordance with the invention even compared to the commercially acceptable control based on a nonylphenol hydrophobe. In this case the deterioration of film performance as the result of water absorption is emphasised by the deterioration of adhesion to a sealed surface.

EXAMPLE 14

This example illustrates the use of a surfactant according to the present invention in preparing a polymer dispersion where the polymer is an alkyd resin.

The materials for the polymer dispersion used were as follows:

| Surfactant (Example 3) | 18 | parts |
|---|---|---|
| Demineralised water | 227 |  |
| Alkyd (soya bean), 97% non-volatiles | 300 |  |

The alkyd was charged into a stirred reactor and heated to 65 C. The maximum allowable stirrer-tip speed was $1 ms^{-1}$. The surfactant was first diluted to 30% by weight solids in demineralized water. The surfactant solution preheated to 65 C. was then charged into the reactor at a constant rate over a 5 minute period and then allowed to mix-in for a further 5 minutes. The stirrer-tip speed was increased to greater than $2 ms^{-1}$. The demineralised water was then charged preheated to 65° C. at a rate of 3 parts per minute until inversion occurs forming the polymer dispersion. Inversion is observed as a rapid change in the viscosity. Once the polymer dispersion was formed the remaining demineralised water was charged to form a 55% weight resin solids dispersion. The remaining demineralised water was charged unheated to assist in cooling the dispersion to room temperature prior to filtering through cheesecloth.

The polymer disperison was measured by Capillary Hydrodynamic Fractionation to be an average particle size of 0.5 microns. The disperison was stable after two weeks at 60° C.

EXAMPLE 15

This is a comparative example which shows the adverse consequences if a surfactant not according to the invention is used. This will be particularly demonstrated in Example 17 where dry film properties are evaluated.

Example 14 was repeated with non-reactive surfactants, nonylphenol ethoxylate (30 moles) sulfate, sodium salt, commercially-available as Alkanate WA20 and the surfactant from Example 9.

A polymer dispersion was successfully formed with Alkanate WA20 with similar particle size and storage stability. The stearyl alcohol ethoxylate (30 moles) sulfate, sodium salt, from Example 9 despite similarities to the present invention failed to produce a satisfactory emulsion. The polymer disperison consisted predominantly of >1 micron multiple emulsion particles which arose from incomplete inversion of the alkyd into an oil-in-water emulsion.

EXAMPLE 16

This is a comparative example which illustrates the benefits in coating applications of alkyd resin dispersions formed using the invention. The conjugated unsaturation of the invention allows the surfactant to take part in the oxidative crosslinking of the alkyd film as evidenced by improved film hardness. Additionally, solvent resistance of films is known to be an indicator of the level of crosslinking in films and so is also a useful measure of the binding of the invention in alkyd films. Where a surfactant is inadequately bound in the film there is a tendency for it to be easily dissolved by solvent with the result that the final film containing the surfactant will show a lower level of performance.

To 200 g of each emulsion from Examples 14 and Example 15, 2.5 g. of 25% ammonia solution was added with stirring to give pH 8–9 and then followed by 6.8 g of Durham (Trade Mark) VX7 mixed metal drier. 100 micron films were cast on glass and allowed to dry for specified times before measurement using a Leitz hardness tester to determine film hardness. Dry time of the alkyd films was measured using a BK Recorder, wet time, surface dry time and through dry time of each film measured. The following table illustrates the advantage given by surfactants produced according to the invention in forming films which improved dry times and film hardness.

| Surfactant | Solvent Resistance Xylene Double Rubs | Times Hardness Hrs/mins Wet Surface Dry Through Dry | Knoop Hardness 80° C. (days dry) | Knoop Hardness 25° C. (days dry) |
|---|---|---|---|---|
| Nonylphenol ethoxylate (30) sulphate, sodium salt | 35 | 1/11<br>1/35<br>15/24 | 2.09<br>3.60<br>3.97 | 0.69<br>1.39<br>1.01 |
| Ocenol 110/130 alcohol ethoxylate (3) sulphate, sodium salt | 47 | –/43<br>1/25<br>14/2 | 2.12<br>3.54<br>3.97 | 1.08<br>1.12<br>1.27 |
| Stearyl alcohol ethoxylate (30) sulphate, sodium salt | 31 | 2/18<br>4/30<br>14/37 | 0.98<br>1.72<br>1.95 | 0.8<br>0.85<br>0.79 |

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

What is claimed is:

1. An aqueous dispersion of polymeric particles wherein the dispersion is formed in the presence of a stabilising amount of an anionic alkoxylate surfactant of the formula I

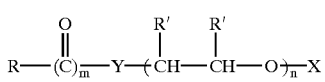

wherein R is a di- or tri-unsaturated $C_{4-22}$ straight or branched hydrocarbon chain, at least two double bonds of said unsaturated chain being conjugated and exhibiting opposite geometric isomerism;

M is 0 or 1;

Y is O or NR';

each R' is independently selected from hydrogen, $C_{1-6}$ alkyl and phenyl; n is 1 to 50; and OX is an anionic group selected from the group consisting of acids or salts of sulphate, succinate, carboxymethyl, maleate, carboxyethyl, alkenylsuccinate, phthalate, sulphoethyl, 3-sulpho-2-hydroxyropyl, sulphopropyl, oxalate and citrate.

2. An aqueous disperison according to claim 1 wherein the dispersion of polymeric particles is prepared by addition polymerization of addition polymerizable monomer.

3. An aqueous dispersion according to claim 2 wherein the addition polymerizable monomer is an ethylenically unsaturated monomer.

4. An aqueous dispersion according to claim 3 where the ethylenically unsaturated monomer is selected from the group consisting of $C_1$—$C_{12}$ alkyl acrylates and methacrylates, (meth)allyl acrylates and methacrylates, butyl methacrylate, stearyl methacrylate, methacrylic acid, methoxypropyl methacrylate, cyclohexyl methacrylate, benzyl methacrylate, hydroxyethyl methacrylate, hydroxypropyl methacrylate, dimethylaminoethyl methacrylate, N-butoxymethyl methacrylamide, N-butoxymethyl acrylamide, glycidyl methacrylate, vinyl acetate, vinyl propionate, styrene and vinyl styrene, vinyl toluene, methoxy styrene and vinyl pyridine, di-butyl maleate and vinyl chloride.

5. An aqueous dispersion according to claim 1 wherein the dispersion of polymeric particles is prepared by dispersion of a condensation polymer.

6. An aqueous disperison according to claim 1 wherein R has the following structure:

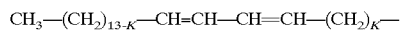

wherein K is 8 or 9.

7. A surfactant according to claim 1 wherein R is derived from linoleyl or linolenyl alcohol or acid by alkoxylation of said alcohol or acid.

8. An aqueous dispersion according to claim 1 wherein at least one R' on the or each —(CHR'—CHR'—O)— unit is hydrogen.

9. An aqueous dispersion according to claim 8 wherein both R' on the or each —(CHR'—CHR'—O)— unit are hydrogen.

10. An aqueous dispersion according to claim 1 where OX is sulphate, carboxymethyl or a salt thereof.

11. An aqueous dispersion according to claim 10 wherein the salt is an amine, ammonium or alkali metal salt.

12. An aqueous dispersion according to claim 1 where R is $C_{10}$–$C_{22}$.

13. An aqueous dispersion according to claim 1 where m is 0.

14. An aqueous dispersion according to claim 1 where Y is O.

15. A method for preparing a coating composition comprising adding an aqueous dispersion according to claim 1 to a coating composition mixture.

16. A method for preparing an aqueous dispersion of polymeric particles comprising conducting an addition or condensation polymerization in the presence of a stabilizing amount of an anionic alkoxylate surfactant of the formula I

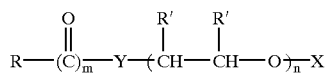

where R is a di- or tri-unsaturated $C_{4-22}$ straight or branched hydrocarbon chain, at least two double bonds of said unsaturated chain being conjugated and exhibiting opposite geometric isomerism;

M is 0 or 1;

Y is O or NR';

each R' is independently selected from hydrogen, $C_{1-6}$ alkyl and phenyl; n is 1 to 50; and OX is an anionic group selected from the group consisting of acids or salts of sulphate, succinate, carboxymethyl, maleate, carboxyethyl, alkenylsuccinate, phthalate, sulphoethyl, 3-sulpho-2-hydroxyropyl, sulphopropyl, oxalate and citrate.

* * * * *